United States Patent
Whitmore, III et al.

(10) Patent No.: US 8,800,569 B2
(45) Date of Patent: Aug. 12, 2014

(54) PATIENT SUPPORT SYSTEM HAVING IMPROVED FIXATION DEVICE MOUNTING FEATURES FOR RADIATION THERAPY

(75) Inventors: Willet F. Whitmore, III, Longboat Key, FL (US); Colin Arne Brue, Orange City, IA (US)

(73) Assignee: Medtec, Inc., Orange City, IA (US)

( * ) Notice: Subject to any disclaimer, the term of this patent is extended or adjusted under 35 U.S.C. 154(b) by 178 days.

(21) Appl. No.: 13/267,540

(22) Filed: Oct. 6, 2011

(65) Prior Publication Data

US 2012/0085356 A1 Apr. 12, 2012

Related U.S. Application Data

(60) Provisional application No. 61/391,803, filed on Oct. 11, 2010.

(51) Int. Cl.
*A61F 5/37* (2006.01)
*A61B 19/00* (2006.01)

(52) U.S. Cl.
CPC ......... *A61F 5/3769* (2013.01); *A61B 2019/206* (2013.01)
USPC ............... 128/870; 128/845; 128/846; 5/601; 5/621; 5/622; 5/637

(58) Field of Classification Search
USPC .............. 128/845, 846, 870; 5/601, 621, 622, 5/637; 378/156, 159
See application file for complete search history.

(56) References Cited

U.S. PATENT DOCUMENTS

| 5,566,681 | A  | * | 10/1996 | Manwaring et al. | 5/622 |
|---|---|---|---|---|---|
| 6,161,237 | A  | * | 12/2000 | Tang et al. | 5/621 |
| 7,073,508 | B2 | * | 7/2006  | Moyers | 128/857 |
| 7,802,576 | B2 | * | 9/2010  | Cuypers et al. | 128/845 |
| 2009/0308400 | A1 | * | 12/2009 | Wilson et al. | 128/845 |

* cited by examiner

*Primary Examiner* — Patricia Bianco
*Assistant Examiner* — Keri J Nelson
(74) *Attorney, Agent, or Firm* — Caesar, Rivise, Bernstein, Cohen & Pokotilow, Ltd.

(57) ABSTRACT

A system including a support panel and a fixation device for use in radiation therapy is disclosed. The support panel comprises a generally planar member that is arranged to be disposed adjacent an apparatus for producing a radiation beam to support a portion of the patient to which the radiation beam will be directed. The fixation device is arranged to be releasably secured to the support panel to hold the portion of the patient's body at a desired position. The fixation device includes attachment components which enable the releasable securement of the fixation device to the support panel without creating any attenuation discontinuities of a radiation beam passing therethrough.

22 Claims, 5 Drawing Sheets

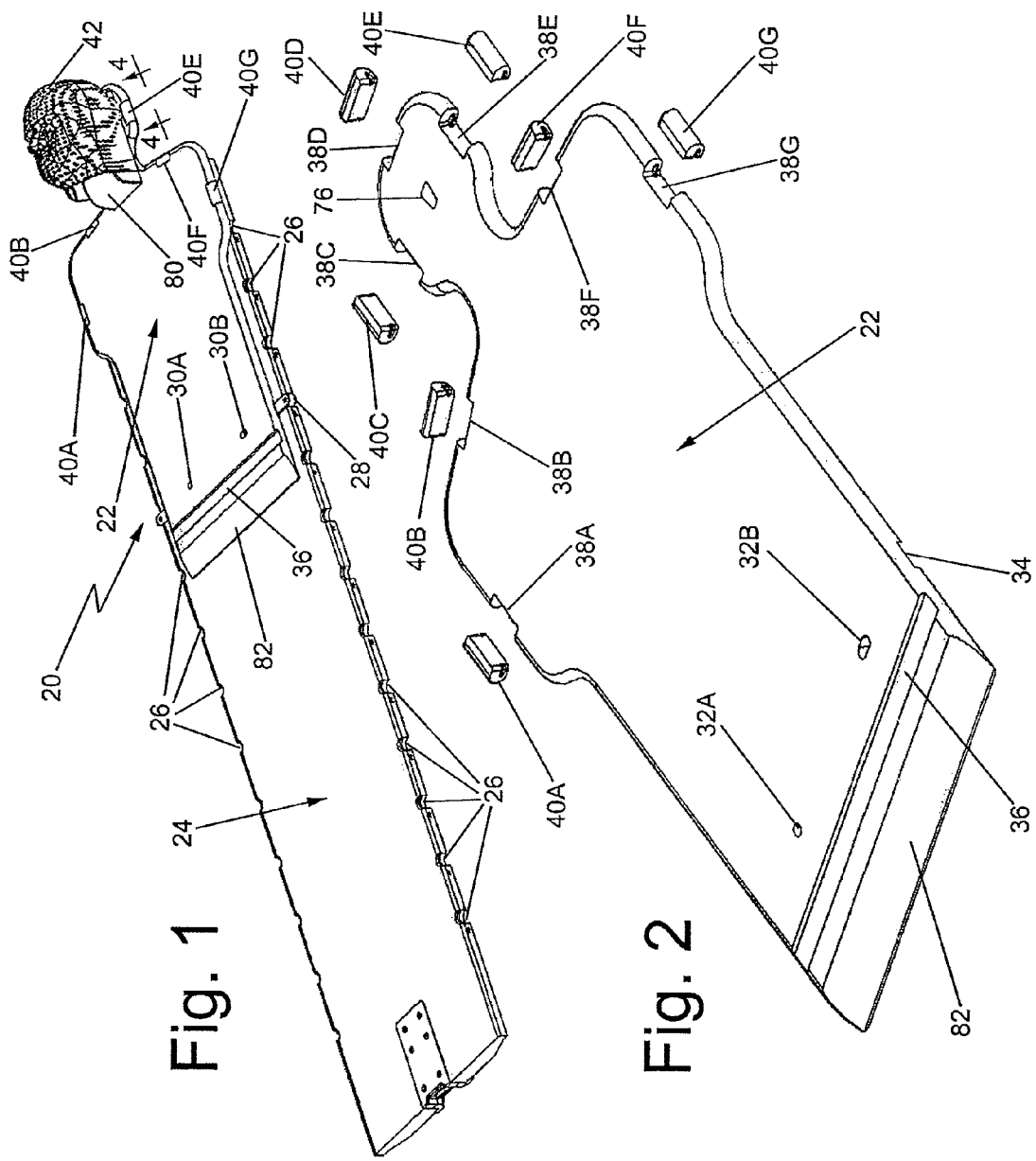

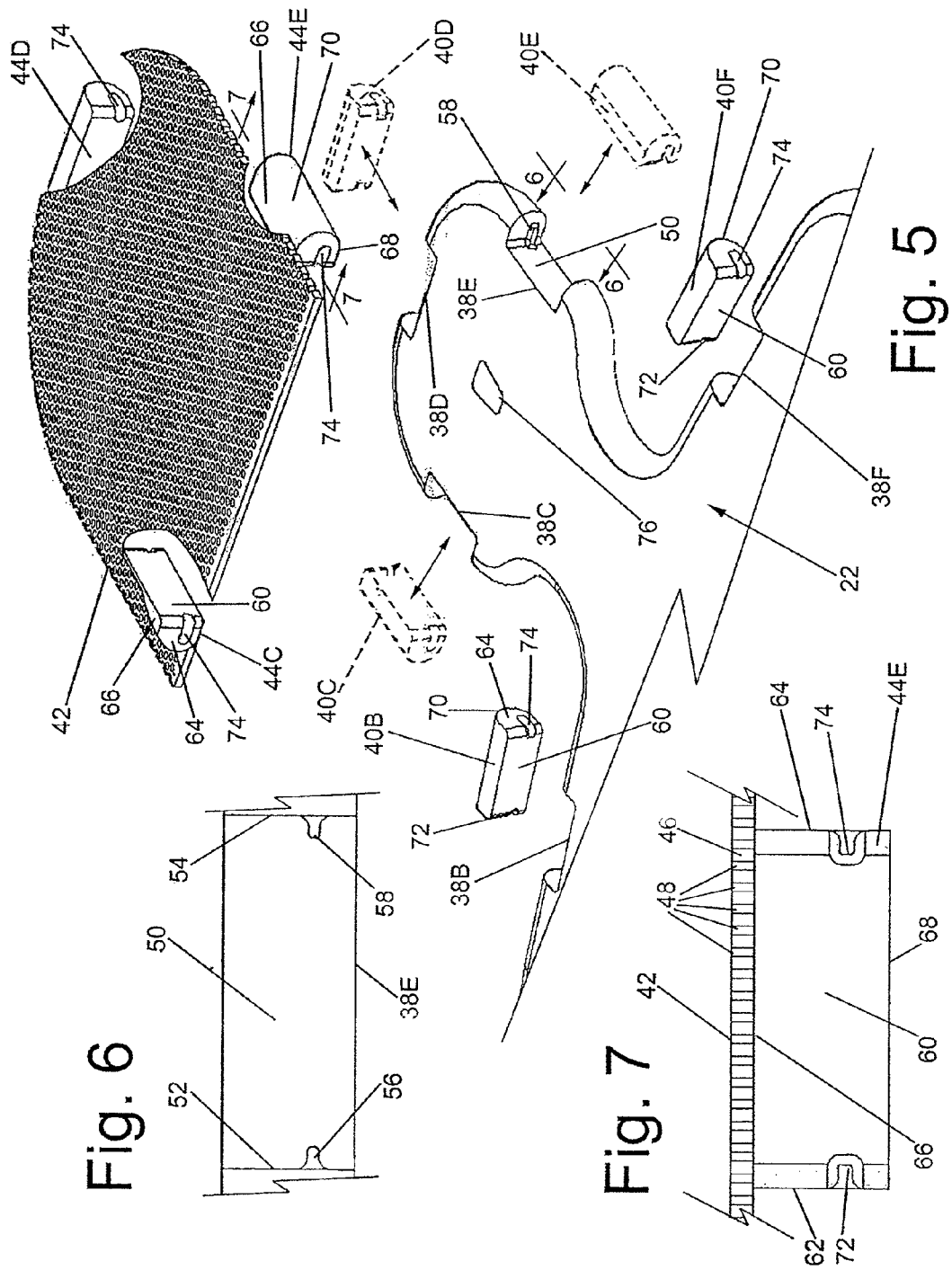

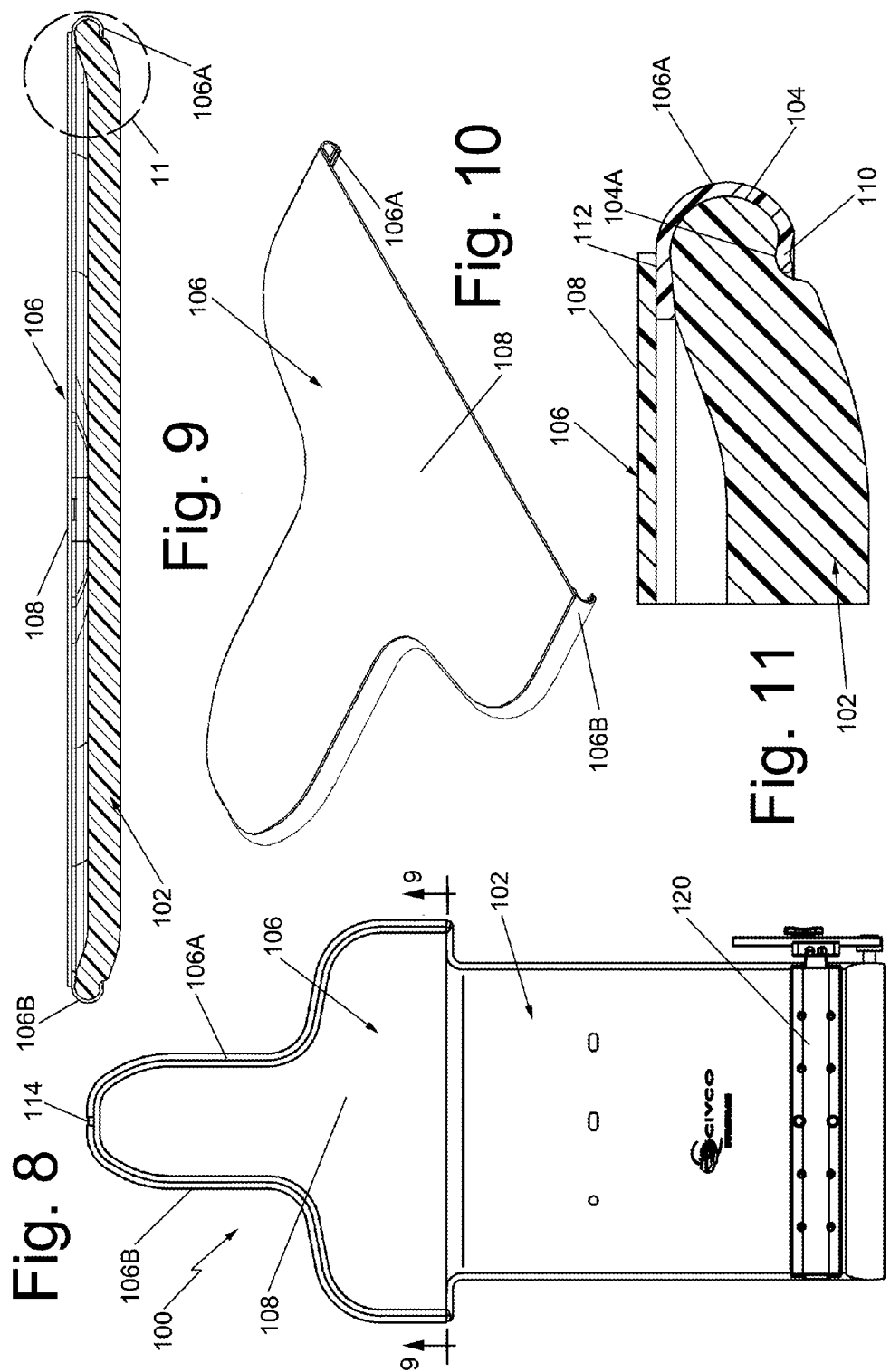

PATIENT SUPPORT SYSTEM HAVING IMPROVED FIXATION DEVICE MOUNTING FEATURES FOR RADIATION THERAPY

CROSS-REFERENCE TO RELATED APPLICATIONS

This utility application claims the benefit under 35 U.S.C. §119(e) of Provisional Application Ser. No. 61/391,803 filed on Oct. 11, 2010 and entitled Patient Support System with Improved Fixation Device Mounting Features for Radiation Therapy, the entire disclosure of which is incorporated by reference herein.

FIELD OF THE INVENTION

This invention relates generally to devices for use in radiation therapy and more particularly to a patient fixation support system for radiation therapy.

BACKGROUND OF THE INVENTION

Patient immobilization is essential for the safety and efficacy of radiation therapy (RT). In particular, patients undergoing RT typically are disposed on a treatment table or couch associated with a LINAC or other the radiation therapy apparatus. Various couch-tops and overlays are commercially available for disposition on the treatment table, with the patient being disposed on the couchtop/overlay. Such couchtops and overlays commonly include indexing features. Fixation or immobilization devices are available for use with the couchtops/overlays to position the patient in the same anatomic position and location on the treatment table as on the planning table (i.e., the table upon which the radiation treatment plan was established). Examples of such patient positioning/fixation devices are head and neck positioning/fixation devices (e.g., thermoplastic masks), breast and thorax positioning/fixation devices, and hip and pelvic region positioning/fixation devices. Many of such devices, as well as other miscellaneous positioning aids, e.g., cushions, wedges, etc., for use on the treatment couchtop/overlay are available from the assignee of this invention, Civco Medical Solutions (hereinafter "CIVCO"), and are shown in its "Radiation Oncology Sourcebook" ©2007. The treatment planning table has matching indexing features to the RT treatment table, and the RT treatment table is registered to the RT treatment beam. This combination enables accurate planning and delivery of radiation therapy.

Other manufacturers also provide couchtops/overlays with various types of indexing systems and positioning/fixation devices to be used with such indexing systems since patient immobilization is essential for the safety and efficacy of radiation therapy.

Some table overlays are commonly employed for extending the head and neck region off the end of a standard built in RT treatment table. Such table overlays are typically of lower density than the treatment table and as uniform in density as possible. Immobilization or fixation devices are secured to these overlays via attachment hardware to hold the particular portion of the patient's anatomy in the desired position for the radiation therapy. The attachment hardware must be employed because the fixation devices must be removable for patient safely and so that the patient may be exactly repositioned at different times for planning and the radiation treatment which may involve multiple sessions.

One type of immobilizing and positioning device used for treating the head and neck region is the thermoplastic mask. This device is a perforated mask that is heated and may then be stretched over the upper torso, head and neck areas and be closely molded to individual anatomy to provide a very secure fit. Typically, the thermoplastic material must be attached to a bracket of some sort to enable handling, fitting of the mask and fixation of the mask to the treatment table. Presently available attachment hardware for the patient positioning and fixation devices that must be used involve brackets and locking features that create focal areas of irregularly shaped (typically plastic) mass that are problematic for both treatment planning and radiation delivery. In particular, the bracket and attachment mechanisms are often in line with the treatment beam and cause attenuation and distortions of the therapeutic beam of energy being delivered that are not easily managed therapeutically. This is a problem for all currently available mask immobilization devices and other related devices that may end up in the treatment path.

Thus, a need presently exists for the solution to the problem of having to image, simulate/plan and treat tumors with RT and having the treatment path obstructed by irregularly shaped and variable density components that are currently used for attaching patient fixation hardware, since such attachment components both attenuate and distort the treatment beam in and undesirable manner that reduces the accuracy of both targeting and dose delivery to the target area within a patient.

The subject invention addresses that need by providing a system including an overlay that eliminates the irregular extra mass of the attachment hardware essentially by attaching the fixation Material or devices directly to the overlay itself. By eliminating these irregular devices of varying thickness and shape and mass (varying density of material in some cases), the imaging is improved, planning becomes simpler because of the reduced calculations required with the cleaner interference platform, and the safety and accuracy of the RT treatment is improved with reduced interference of the treatment beam.

All references cited and/or identified herein are specifically incorporated by reference herein.

SUMMARY OF THE INVENTION

In accordance with one aspect of the invention there is provided a system for use with a fixation device, e.g., a headrest, face mask, etc., for supporting a patient for radiation therapy. The system comprises a support panel and at least one attachment member. The support panel comprises a generally planar member arranged to be disposed adjacent an apparatus, e.g., a LINAC, for producing a radiation beam to hold a portion, e.g., the head and neck, of a patient at a fixed position on the support panel to enable the radiation beam to be directed to that portion of the patient. The portion of the patient to which the radiation beam will be directed is to be held at the fixed position on the support panel by use of a fixation device. The at least one attachment member is arranged to be fixedly secured to the fixation device. The support panel has at least one attachment region of a predetermined shape, e.g., a recess. The at least one attachment member has a portion of a mating shape to the at least one attachment region and is constructed so that the at least one attachment member may be mating releasably secured to the at least one attachment region, whereupon the mating portions exhibit a uniform density which does not result in any attenuation discontinuities of a radiation beam passing therethrough.

In accordance with another aspect of this invention there is provided a support panel for use with a fixation device for supporting a patient for radiation therapy. The support panel is constructed like that discussed above. The fixation device has an attachment member fixedly secured thereto. The attachment member of the fixation device has a portion of mating shape to the at least one attachment region of the support panel and is constructed so that the attachment member may be mating releasably secured to the at least one attachment region, whereupon the mating portions thereof exhibit a uniform density which does not result in any attenuation discontinuities of a radiation beam passing therethrough.

In accordance with still another aspect of this invention a system for supporting a patient for radiation therapy is provided. That system comprises a support panel and a fixation device. The support panel comprises a generally planar member arranged to be disposed adjacent an apparatus for producing a radiation beam to hold a portion of a patient at a fixed position on the support panel to enable the radiation beam to be directed to that portion of the patient, the portion of the patient being held at the fixed position on said support panel by use of the fixation device. The support panel has a peripheral edge of a predetermined shape, which is bulbous in cross section and has an undercut surface. The fixation device comprises a flexible planar thermoplastic sheet having two opposed side portions, a first attachment member fixedly secured to one of the side portions and a second attachment member fixedly secured to the other of the side portions. The first attachment member is arranged to be releasably secured to a first portion of the periphery of the support panel and has a shape to matingly receive the first portion of the periphery of the support panel therein. The second attachment member is arranged to be releasably secured to a second portion of the periphery of the support panel and has a shape to matingly receive the second portion of the periphery of the support panel therein. Each of the attachment members includes a peripheral free edge portion arranged to be snap-fit into a respective portion of the undercut surface of the peripheral edge of the support panel to hold the fixation device at a fixed position on the support panel. The fixation device is arranged to be removed from the support panel when desired and then to be resecured to the support panel at the fixed position when desired. The fixation device exhibits a uniform density, which does not result in any attenuation discontinuities of a radiation beam passing therethrough.

In accordance with yet another aspect of this invention a fixation device for use with a support panel for supporting a patient for radiation therapy is provided. The support panel comprises a generally planar member arranged to be disposed adjacent an apparatus for producing a radiation beam to hold a portion of a patient at a fixed position on the support panel to enable the radiation beam to be directed to that portion of the patient. The support panel has a peripheral edge of a predetermined shape which is bulbous in cross section and has an undercut surface. The fixation device comprising a flexible planar thermoplastic sheet having two opposed side portions, a first attachment member fixedly secured to one of the side portions and a second of attachment member fixedly secured to the other of the side portions. The first attachment member is arranged to be releasably secured to a first portion of the periphery of the support panel and has a shape to matingly receive the first portion of the periphery of the support panel therein. The second attachment member is arranged to be releasably secured to a second portion of the periphery of the support panel and has a shape to matingly receive the second portion of the periphery of the support panel therein. Each of the attachment members includes a peripheral free edge portion arranged to be snap-fit into a respective portion of the undercut surface of the peripheral edge of the support panel to hold the fixation device at a fixed position on the support panel. The fixation device is arranged to be removed from the support panel when desired and then to be resecured to the support panel at said fixed position when desired. The fixation device exhibits a uniform density, which does not result in any attenuation discontinuities of a radiation beam passing therethrough.

DESCRIPTION OF THE DRAWING

FIG. 1 is an isometric view of one exemplary embodiment of a couchtop overlay and associated components forming a portion of a patient support system constructed in accordance the subject invention, with the couchtop overlay being shown disposed on a conventional radiation therapy couchtop;

FIG. 2 is an enlarged exploded isometric view of the overlay shown in FIG. 1;

FIG. 5 is an enlarged exploded isometric view of a portion of the couchtop overlay of FIG. 1 and another fixation device, e.g., a thermoplastic mask, arranged to be releasably secured to the overlay;

FIG. 6 is an enlarged side elevation view taken along line 6-6 of FIG. 5;

FIG. 7 is an enlarged side elevation view taken along line 7-7 of FIG. 5;

FIG. 8 is a top plan view of another embodiment of a couchtop overlay (support panel) and a fixation device constructed in accordance with the subject invention;

FIG. 9 is an enlarged transverse sectional view taken along line 9-9 of FIG. 8;

FIG. 10 is an isometric view of the fixation device shown in FIG. 8; and

FIG. 11 is an enlarged sectional view of a portion of the couchtop overlay (support panel) and fixation device shown within the area bounded by the circle designated by the number 11 in FIG. 9.

DETAILED DESCRIPTION OF THE PREFERRED EMBODIMENT

Figure 3:
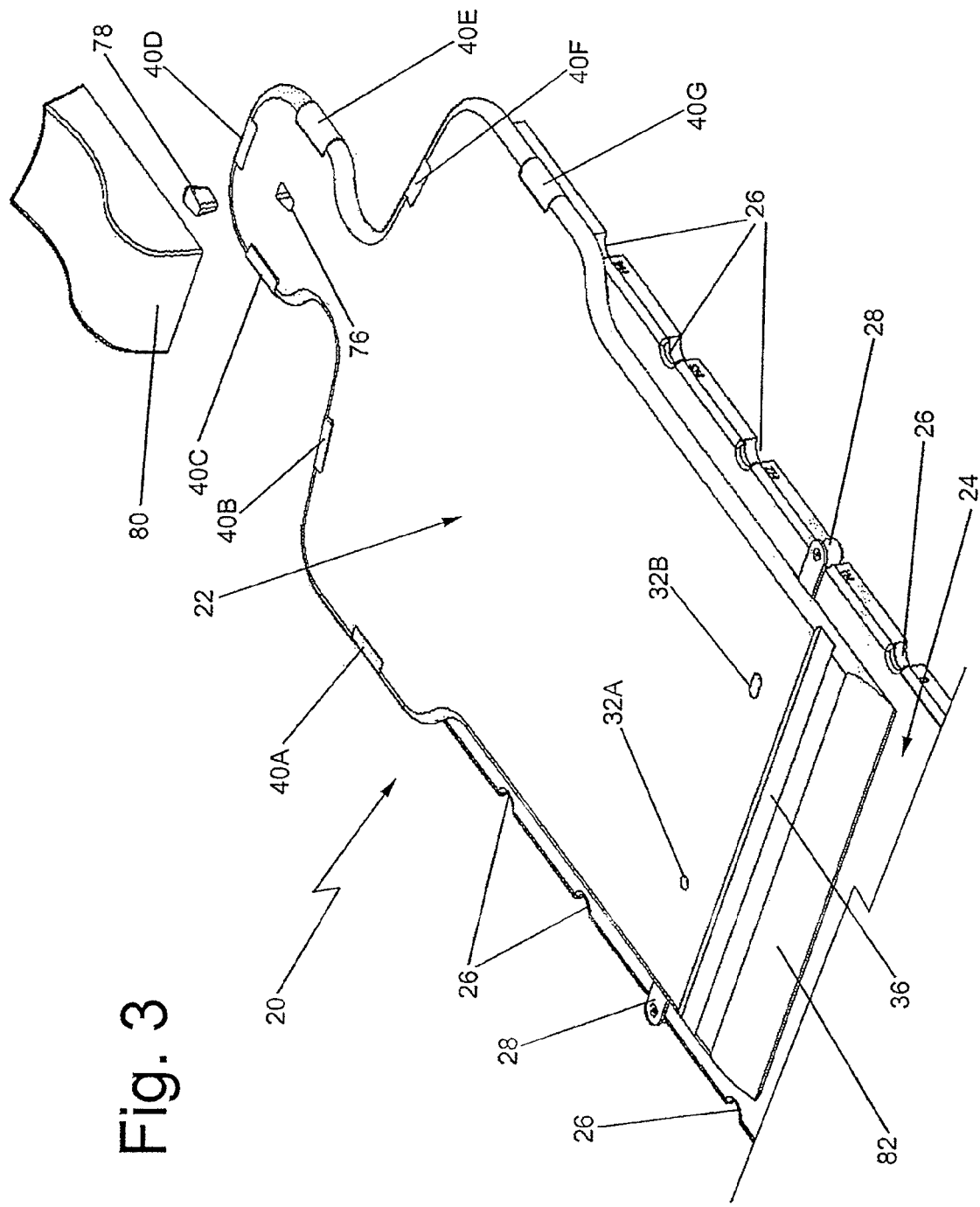
FIG. 3 is an enlarged exploded isometric view of the couchtop overlay and associated components shown in FIG. 1.

Referring now to the various figures of the drawing wherein like reference characters refer to like parts, there is shown in FIG. 1 an overlay 22 of a patient support system 20 constructed in accordance with this invention for use in providing radiation therapy to a patient. The overlay 22 is arranged to be used with other components of the system 20 (to be described later). Those other components form a portion of or are fixedly secured to fixation material(s)/devices(s), such as, pads, masks, bridges, brackets, etc. for immobilizing a desired portion of the anatomy of the patient. To that end, the overlay 22 is arranged to be disposed on any conventional couchtop 24, which in turn is disposed on a cradle and docking station associated with radiation therapy apparatus, e.g., a LINAC (not shown). In the exemplary embodiment shown the overlay 22 is shown mounted on a couchtop 24 like those commercially available from CIVCO Medical Products Company. Those CIVCO treatment couchtops make use of an array of equidistantly spaced indexing points 26 running down the side of the couchtop/overlay. A two-pin LOK-BAR™ member 28, also sold by CIVCO, is arranged to be connected to the couchtop at any of the indexing points 26. The two-pin member 28 is an elongated bar that includes two pins 30A and 30B projecting upward from it to interface (be received in). The pins 30A and 30B are arranged to be received in corresponding holes in various patient positioning/fixation devices sold by CIVCO. To that end, in prior art applications, the particular patient positioning/fixation device is mounted on the LOK-BAR™ member 28 by disposing it on the member 38 so that the two-pins 30A and 30B are received within corresponding apertures in the positioning/fixation device. By indexing the patient positioning/fixation device(s) to the same indexing points for every radiation treatment one can be assured of increased target accuracy and patient throughput. In the subject invention, the two pin bar 20 serves to releasably secure the overlay 22 to the couchtop at any desired position thereon, with that position being established by the indexing points 26. Other means, to be described later, which form a portion of the overlay 22, serve to effect the releasable connection of the patient positioning/fixation device(s) to the overlay.

As best seen in FIGS. 1 and 2, the overlay 22 is sized to accommodate the head, neck and upper torso of the patient, with the remainder of the patient being disposed on the couchtop 24. The overlay has a general profile of the shape of the upper portion of a human being. The overlay 22 is arranged to be positioned on the couchtop 24 at any desired position thereon, e.g., with the head and neck portion of the overlay 22 extending beyond the forward end of the couchtop 24. The pins 30A and 30B of the bar 28 are received in respective holes 32A and 32B (FIG. 2) in the overlay 22 to releasably secure the overlay 22 to the couchtop 24. To that end the overlay 22 also includes a transverse channel 34 in its lower surface to accommodate the bar 28. In addition, the overlay 22 includes another transversely extending recess or channel 36 in its top surface adjacent the lower end of the overlay for receipt of a hold-down bar or strap (not shown).

The overlay 22 is formed of any suitable strong and lightweight material. One particularly suitable material is high density plastic foam having a thin KEVLAR® aramid external coating or skin. The overlay can be formed of other materials as well, e.g., low density plastics, solid carbon fiber, etc.

Irrespective of the particular material(s) making up the overlay 22, it is constructed and arranged to eliminate the irregular extra mass of the attachment hardware of conventional fixation/positioning (immobilization) devices. This is accomplished essentially by attaching such device(s) directly to the overlay itself. One way this is achieved is by providing appropriately spaced and located attachment regions in the form of recesses or cutouts in the overlay, and also providing matching attachment members in the form of insert components of the identical material as the overlay, and which insert components have been fixedly secured, e.g., adhesively bonded or otherwise fastened, to the patient fixation device(s). In addition, other similarly constructed insert components are preferably provided for filling each cutout that doesn't have any fixation device connected to it so that there are no gaps in the overlay which could result in an discontinuity in the attenuation produced by the overlay as the radiation beam traverses it.

Each cut-out acts as a connector element while each insert acts as a respective and cooperating connector element to enable them to be releasably secured together. For example, in the exemplary preferred embodiment shown herein, the cut-outs and inserts fit or mate together, like pieces of a puzzle. To facilitate their connection the cutouts and inserts may be configured so that one element, e.g., the insert, slides in the cut-out on a track-like member or rib (to be described later) in a manner similar to the way a tongue and groove arrangement fits together. Alternatively, the cut-outs and inserts may make use of other alignment features, so long as the particular alignment feature utilized enables accurate re-positioning of the insert in the cut-out to achieve a fully aligned restoration of the overlay with the cut-out space being perfectly (completely) filled so that there are no gaps which could result in an discontinuity in the attenuation produced by the overlay as the radiation beam traverses it.

Thus, as best seen in FIG. 2 the overlay includes a plurality of recesses or cut-outs 38A, 38B, 38C, 38D, 38E, 38F and 38G disposed at various locations about the periphery of the overlay 22. Each of the recesses 38A-38G is of the exact same construction as any other and each is arranged to cooperate with an associated, mating shaped insert. The inserts come in two types, depending upon the use to which they will be put, although both types of inserts are of identical construction. In this connection one type of insert, referred to hereinafter as a "filler piece", is provided to merely serve as a means for filling the space formed by a cutout. Thus when a filler piece is mounted in a cutout the portion of the overlay at which the cut-out and filler piece are located exhibits a smooth continuous periphery without any discontinuities. The other variety of insert, referred to hereinafter as a "filler-connector", is provided to serve as the means for releasably mounting a fixation device to the overlay. To that end the filler-connector is fixedly secured to or forms a portion of the fixation device.

Exemplary "filler pieces" are shown clearly in FIG. 2 and are designated as 40A, 40B, 40C, 40D, 40E, 40F and 40G. As mentioned earlier, each filler piece is of identical construction so that any one can be disposed in any cut-out. Moreover, each filler piece is formed of the same material as that making up the overlay and the outer profile and contour of each piece is such that when it is located within any cut-out it forms a smooth, continuous surface with the surface of the overlay like shown in FIG. 3. By so doing no sharp edges or projections are exposed, which edges or projections could possibly result in injury to the patient. The details of each of the cut-outs and filler pieces will be described later. Suffice it for now to state that each of the filler pieces 40A-40G is arranged to be readily removed from its associate cut-out to enable a fixation material/device to be releasably secured to that cut-out. To that end, each fixation device which is to be used with the overlay includes a "filler-connector" fixedly secured to it. Each filler-connector is identical in construction to any of the filler pieces 40A-40G.

Figure 4:
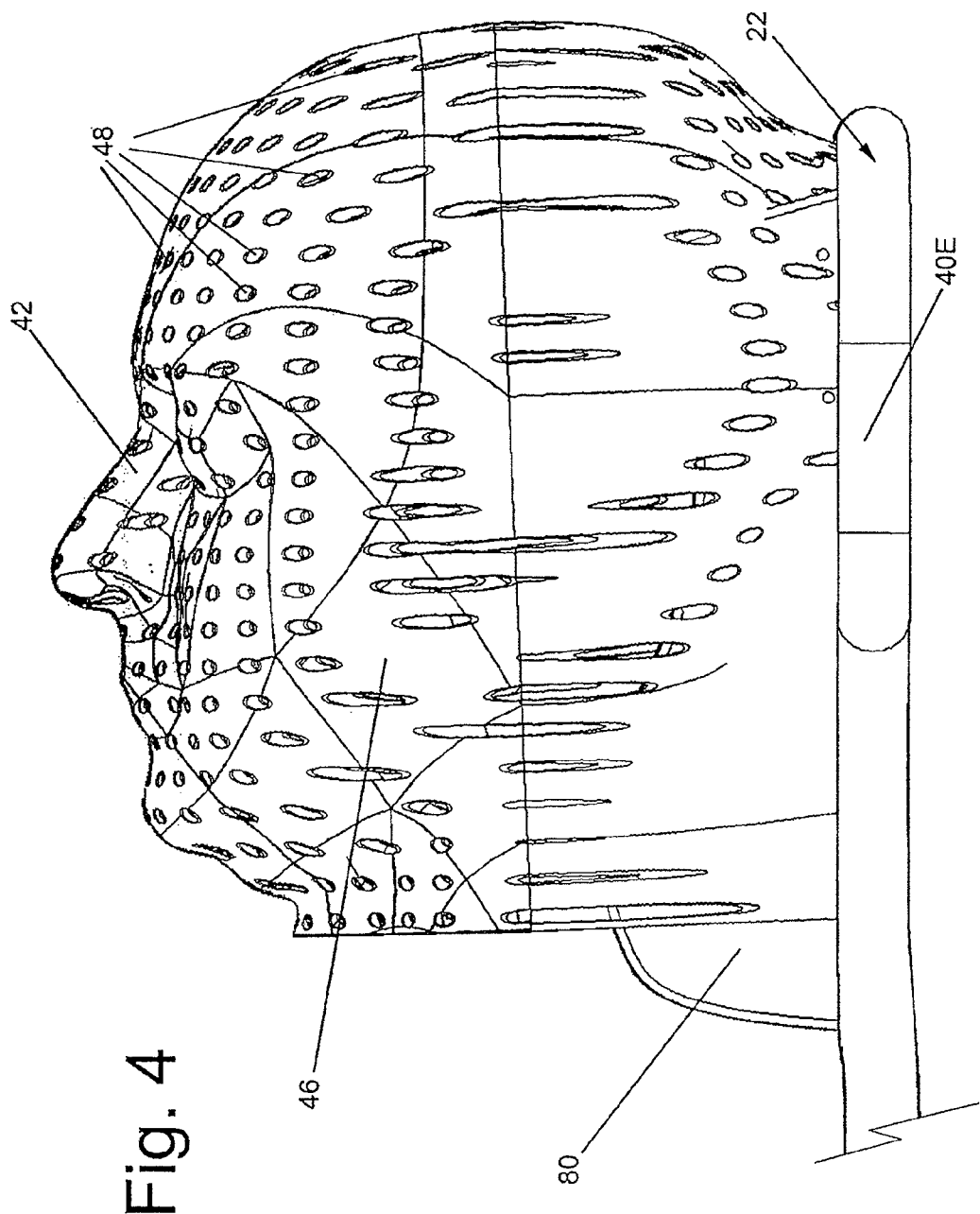
FIG. 4 is a greatly enlarged side elevation view taken along line 4-4 of FIG. 1.

In FIG. 5 there is shown one exemplary embodiment of a fixation device, i.e., a thermoplastic mask 42, including three filler connectors 44C, 44D and 44E constructed in accordance with this invention. The mask 42 is of generally conventional construction, except for the filler connectors 44C, 44D and 44E. To that end it includes a web 46 of thermoplastic material having a multitude of apertures 48 therein. The web is arranged to be heated to enable it to soften so that it can be placed over the head and face of a patient and stretched to the contour of the patient's head and face, as best seen in FIGS. 1 and 4. When the mask has cooled it will then be custom fit to accommodate the patient's head to immobilize the patient's head during radiation therapy. The securement of the contoured mask to the overlay 22 is accomplished by use of the three filler connectors 44C, 44D and 44E. Each filler connector 44C, 44D and 44E is of identical construction to the others and to the filler pieces 40A-40G. Each filler-connector, like each filler piece, is arranged to be disposed in and secured to any of the cut-outs in the same manner as that the filler pieces are disposed in and secured to the cutouts. In the case of the thermoplastic mask 42, its connectors 44C, 44D and 44E are arranged to be disposed in the cutouts 38C, 38D and 38E, respectively, after the filler pieces 40C, 40D and 40E (shown in phantom in FIG. 5) have been removed to expose those cut-outs.

Referring now to FIGS. 6 and 7, the details of the cutouts and the inserts will now be discussed. In particular, FIG. 6 is an elevation view of cut-out or recess 38E, but could be of any of the cutouts, since all are identical. Thus, as can be seen the cutout 38E basically comprises a generally planar back wall 50 and a pair of generally planar sidewalls 52 and 54. Each of the sidewalls extends perpendicularly to the plane of the back wall 50. A pair of protrusions in the form of generally linear ribs 56 and 58 project outward from the respective sidewalls 52 and 54. The ribs 56 and 58 serve as rails for guiding and supporting the insert in the cutout. To that end, the leading edge of each rib is rounded to facilitate the introduction of the rib into a respective slot or groove in the insert.

Turning now to FIG. 7 there is shown an elevation view of a typical insert. In this case it is insert 44E, but it could be any of the inserts, be they filler pieces or filler connectors, since as mentioned earlier all are identical. The insert 44E includes a generally planar front wall 60, a pair of generally planar sidewalls 62 and 64, a generally planar top wall 66, a generally planar bottom wall 68 and an arcuate rear wall 70 (FIG. 5). The contour of the rear wall 70 matches the contour of the peripheral edge of the overlay 22 such so that when it is disposed within its cutout the rear wall of the insert will be flush with the contiguous portion of the periphery of the overlay 22. At the same time, the top and bottom walls of the insert 44E will be flush with the contiguous portions of the top and bottom surfaces, respectively, of the overlay. The outer corners of the insert, i.e., the area at which the sidewalls 62 and 64 of the insert merge with its front wall 60 are rounded. A pair of slots or grooves 72 and 74 of complementary size and shape to the ribs 56 and 58 and having chamfered or rounded edges project inward along the sidewalls 62 and 64, respectively, from the corners of the insert. Thus, the insert 44E can be readily introduced into the cutout 38E by juxtaposing it so that it is in the plane of the overlay, with the leading end of its grooves 72 and 74, aligned with the leading ends of the ribs 56 and 58, respectively. The insert 44E can then be pushed inward until its front wall 60 abuts the back wall 50 of the cutout 38E so that the insert will be perfectly fit within the cutout and held in place by frictional securement. If desired, some other mechanism (not shown), e.g., a detent, could be used to releasably secure the insert within the cutout. In any case, when the insert is fully within its cutout the outer surface of the insert will be flush with the contiguous surfaces of the overlay and there will be no discontinuities in the amount of attenuation of any therapy beam passing through the insert/cutout as compared to the therapy beam passing through an adjacent portion of the overlay.

Any fixation device or any other device which is desired to be releasably secured to the overlay 22 can be made so that it includes one or more inserts, constructed as discussed above, either as a portion of the device or fixedly secured thereto to mount that device on the overlay. Moreover, each cutout of the overlay that does not serve to mount a device thereon is preferably filled with an insert.

It should be pointed out that the exemplary embodiment of the support panel or overlay shown and described above makes use of a pair of linear protrusions in each cutout. The protrusions extend generally parallel to the plane of the overlay and are located slightly below the centerline of the overlay to engage matching grooves in the inserts. Thus the inserts are introduced into the cutouts laterally from the side in the plane of the overlay. An alternative arrangement that may prove superior in some applications would be to have the protrusions angled diagonally. In that case the inserts would have reciprocal diagonal grooves and would be inserted beginning out of plane of the overlay, but also from the side. In fact, the subject invention contemplates use of other arrangements to guide and hold the inserts in place within the cutouts, e.g., only a single rib or rail and a correspondingly shaped groove can be used. Further still, while not preferred, the subject invention contemplates reversal of the cutouts and inserts, e.g., the overlay may constructed so that instead of having cutouts at the various locations about its periphery, it includes projections at those locations. In such a case each of the inserts which is connected to or forms a portion of a fixation device would be constructed to include a recess of mating size and shape to the projections so that it can be mating releasably secured thereto to releasably mount the fixation device to the overlay.

Turning back to FIGS. 2 and 3 it can be seen that in the center of the head support portion of the overlay 22, there is a cutout 76 with tapered sides and an asymmetrical shape. A filler piece or plug 78 of matching shape is provided for residence within the cutout. The plug 78 is arranged to be fixedly secured, e.g., adhesively bonded, to the underside of a fixation attachment, e.g., a headrest 80. The plug 78 is arranged for receipt within the cutout 76 to releasably secure the headrest 80 onto the head support portion of the overlay 22. The asymmetrical shape of the plug 78 forces the user to correctly orient the fixation attachment 80 and achieve a perfect re alignment of the surfaces once the filler piece is inserted. If no headrest or other device is to be secured to the head support portion of the overlay, a plug 78 by itself will be disposed within the cutout 76. Thus, there will be no discontinuity in the attenuation of the radiation beam as it traverses the cutout 76 of the overlay.

As can also be seen in FIGS. 1 and 2 the lower end of the overlay is tapered at 82 to provide a somewhat continuous surface or smooth transition from the top surface of the couchtop to the top surface of the overlay in the interest of patient comfort.

Uniform and low density of fixation and support materials is deemed essential for the planning and delivery of radiation therapy. The embodiment of the invention shown in FIGS. 1-7, and variants thereof, optimizes the attachment of thermoplastic and other fixation devices in this regard by making cutouts in the patient support structure, securing the fixation devices to parts made of materials identical to the cutouts that also are a perfect fit to the cutouts. And, using these inserts to secure the fixation devices to the support structure so that the support structure and all surfaces are then fully restored to the original shape and density with the fixation devices securely mounted.

Referring now to FIGS. 8-11 another embodiment of a system 100 for supporting a patient for radiation therapy is disclosed. This system, like the system 20 shown in FIGS. 1-7, eliminates the beam-attenuating irregularities of current fixation mechanisms. However, the system 100 shown in FIGS. 8-11 achieves that end by utilizing a support panel or overlay 102 that does not include any recesses or cut-outs, like those of FIGS. 1-7 for receipt of matingly shaped attachment members (connectors). Instead, the support panel 102 of the system 100 has a continuous uniformly shaped peripheral edge 104. That edge is arranged to have releasably secured to it a frame of a fixation device 106 also constructed in accordance with this invention. In the exemplary embodiment shown in FIGS. 8-11, the fixation device 106 comprises a mask for holding the head and shoulders of a patient. Other variants are contemplated for holding other portions of the body of a patient. In any case, the fixation device 106 includes a flexible sheet of a thermoplastic material 108. For applications requiring immobilization of the head of a patient the thermoplastic sheet 109 is similar in construction to the sheet 42 of the mask described above with respect to the system 20. To that end, the sheet 106 has a pair of side portions to which respective ones of a pair of attachment members 106A and 106B are fixedly secured. The attachment members 106A and 106B together form a split frame that is arranged to be releasably secured, e.g., snap fit, to the corresponding portions of the peripheral edge 104 of the support panel 102 to releasaby mount the fixation device to the support panel. To that end, the split frame has a uniform shape along the entire portion of the peripheral edge of the support panel to which it attaches. The details of the split frame will be described shortly. The support panel 102, which will also be described shortly, has a uniform shape along the attachment area, resulting in a uniform geometry all through the area of interest when the fixation device is attached to the support panel.

Referring now to FIG. 8, it can be seen that the support panel or overlay 102 is similar in construction to the overlay panel 22, except for the omission of the attachment recesses. In the interest of brevity the common features of the support panels 22 and 102 will be given the same reference numbers and the details of the construction and operation of those components will not be reiterated. The support panel 102 is arranged to be disposed on a couchtop 24 and releasably secured thereto via a latch assembly 120, which is disposed within the recess 36 in the support panel. In the interest of brevity the details of the components making up the latch assembly will not be described.

The support panel 100 can be formed of any material, such as that described with reference to the embodiment of the overlay 22.

As mentioned above the peripheral edge 104 of the support panel 102 is continuous and smooth along its entire length. As best seen in FIGS. 9 and 11 the peripheral portion 106 of the support panel extends upward at a slight acute angle to the plane of the panel 102 and terminates in a bulbous shaped peripheral edge 104. This bulbous shape extends along the entire length of the support panel. The thickness of the support panel at its periphery is slightly thinner than at other portions thereof to form an undercut region or surface 104A, which extends on the underside of the peripheral edge of the panel slightly inward from the outermost portion of that peripheral edge. The undercut surface 104A is slightly arcuate (concave) in shape.

Referring now to FIG. 10 the details of the fixation device or mask 106 will now be described. As mentioned above that device includes a flexible thermoplastic sheet 108, which is constructed similarly to the sheet 42. As mentioned above the attachment members 106A and 106B together form a split frame for releasably securing or mounting the fixation device on the support panel 102. Both attachment members are of identical construction, albeit being mirror images of each other. Each attachment or frame member is a separate component, which formed of any suitable material, e.g., a thermoplastic. As best seen in FIG. 11, each attachment member is of a generally C-shaped profile (cross section) having a free edge portion in the form of a slightly curved tab 110. The hollow interior of each C-shaped frame member is sized to closely accommodate the peripheral edge 104 of a portion of the support panel therein, with the tab 110 extending into the undercut recess 104A. The top surface 112 of each of the attachment members, 106A and 106B, is fixedly secured to the undersurface of the thermoplastic sheet 108 at the periphery thereof. When so attached there is a very slight gap 114 between the ends of the two confronting attachment members as shown in FIG. 8.

Since the sheet 108 is thermoplastic, it can be heated to make it stretchable and conformable. Inasmuch as the two attachment members are fixedly secured to opposite sides of the sheet 108, with a slight gap 114 between them, the attachment members can be grasped and pulled apart after the thermoplastic sheet has been heated to conform the sheet to the contours of the patient's head and shoulders and to secure to fixation device 106 to the to support panel or overlay 102. To that end, the heated fixation device is stretched over the portion of the patient to be immobilized, e.g., the patient's head and shoulders, and each attachment member is secured to the corresponding portion of the support panel. In particular, each attachment member is juxtaposed with respect to the portion of the peripheral edge of the support panel to which it is to be attached so that the tab 110 and contiguous portion of the C-shaped profile of the frame flexes outwards as it moves past the bulbous (rounded) edge of the support panel, until the tab 110 comes to rest in the undercut (thinner) section or surface 104A of the support panel 102. This mechanism provides a natural snap-fit or attachment of the fixation device to the support panel at the desired position and so that the fixation device is resistant to accidental displacement. Such action is accomplished without any non-uniform geometry components in the latching region.

The frame being split into two (or possibly more) pieces allows the mask to be removed and reapplied to a patient once the mask is fully cured and hardened. The pieces of the split frame allow enough motion for the mask's sides to be pulled outwards from the support panel to detach, to enable the mask to be lifted off the patient. When reattaching the mask on the patient, e.g., at some subsequent radiation treatment, the two attachment members or pieces of the frame are pulled outwards while the flexible sheet of the mask is being placed down over the patient, and then snapped inwards over the edge of the support panel to reattach the mask to the support panel.

As should be appreciated by those skilled in the art the embodiment of the system shown in FIGS. 8-11, and variants thereof optimize the attachment of thermoplastic masks and other fixation devices by utilizing a thin plastic split frame that attaches to the support panel and has the thermoplastic sheet for conformance to a portion of the patient's body, e.g., the patient's head, bonded to the frame. This frame has a shape that is closely similar to the edge of the support panel to attempt to keep a uniform geometry between the support panel and frame all the way along the edge of the attachment area. The frame attaches to the support panel utilizing a spring-tension C-shape in the plastic material. The split frame allows for ease of handling the thermoplastic sheet, while still allowing the frame to be released via outward motion, when desired for disconnection and reconnection.

In conclusion it should be clear that the systems of this invention address the problem of having to image, simulate/plan and treat tumors with radiation therapy (RT) and having the treatment path obstructed by irregularly shaped and variable density components that are currently used for attaching patient fixation hardware. The conventional prior art attachment hardware both attenuates and distorts the treatment beam in and undesirable manner that reduces the accuracy of both targeting and dose delivery to the target area within a patient. By eliminating these irregular devices of varying thickness and shape and mass (varying density of material in some cases), the imaging is improved, planning becomes simpler because of the reduced calculations required with the cleaner interference platform, and the safety and accuracy of the RT treatment is improved with reduced interference of the treatment beam.

Without further elaboration the foregoing will so fully illustrate our invention that others may, by applying current or future knowledge, adopt the same for use under various conditions of service.

We claim:

1. A system for use with a fixation device for supporting a patient for radiation therapy, said system comprising a support panel and plural inserts, at least one of said inserts being an attachment member arranged for attaching a fixation device to said support panel, said support panel being arranged to be disposed adjacent an apparatus for producing a radiation beam to hold a portion of a patient at a fixed position on said support panel to enable the radiation beam to be directed to that portion of the patient, the portion of the patient being held at the fixed position on said support panel by use of the fixation device, said attachment member being arranged to be fixedly secured to the fixation device, said support panel comprising a generally planar member having a peripheral edge and plural recesses, each of said recesses being of a predetermined shape and being located in said edge, each of said inserts having an edge surface and a portion of mating shape to said recesses, and being contiguous with said edge surface, each of said inserts being constructed to enable it to be mating releasably secured in a respective one of said recesses to completely fill said recess with said edge portion of said insert being flush with said peripheral edge of said support panel, whereupon the mating portions thereof exhibit a uniform density which does not result in any attenuation discontinuities of a radiation beam passing therethrough.

2. The system of claim 1 wherein at least one of said insets comprises a filler member.

3. The system of claim 1 wherein one of said recesses and said inserts comprising elongated rib and the other of said recesses and said inserts comprising an elongated groove, said rib being arranged to be slid into said groove to effect the mating releasable securement of said at least insert to said recess.

4. The system of claim 3 wherein said rib and said groove extend in a line parallel to the plane of said support member.

5. The system of claim 3 wherein said rib and said groove extend in a line at an acute angle to the plane of the support member.

6. The system of claim 1 wherein said support panel is formed of high density plastic foam having an aramid external skin.

7. A support panel for use with a fixation device for supporting a patient for radiation therapy, said support panel being arranged to be disposed adjacent an apparatus for producing a radiation beam to hold a portion of a patient at a fixed position on said support panel for receipt of the radiation beam, the portion of the patient being held at the fixed position on said support panel by use of the fixation device, the fixation device having an attachment member fixedly secured thereto, said support panel comprising a generally planar member having a peripheral edge and at least one recess of a predetermined shape in said edge, the attachment member of the fixation device having an edge surface and a portion of mating shape to said at least one recess, the portion of the at least one attachment member being contiguous with the edge surface of the at least one attachment member, one of said at least one recess and the at least one attachment member comprises an elongated rib and the other of said at least one recess and the at least one attachment member comprises an elongated groove, said rib being arranged to be slid into said groove to effect the mating releasable securement of the at least one attachment member in said at least one recess to completely fill said at least one recess with said edge portion of the at least one attachment member being flush with said peripheral edge of said support panel, whereupon the mating portions thereof exhibit a uniform density which does not result in any attenuation discontinuities of a radiation beam passing therethrough.

8. The support panel of claim 7 wherein said at least one recess is located in the periphery of said support panel.

9. The support panel of claim 7 wherein said system includes plural recesses.

10. The support panel of claim 7 wherein said rib and said groove extend in a line parallel to the plane of said support member.

11. The support panel of Claim 7 wherein said rib and said groove extend in a line at an acute angle to the plane of the support member.

12. The support panel of claim 7 wherein said support panel is formed of high density plastic foam having an aramid external skin.

13. A system for supporting a patient for radiation therapy, said system comprising a support panel and at a fixation device, said support panel comprising a generally planar member being arranged to be disposed adjacent an apparatus for producing a radiation beam to hold a portion of a patient at a fixed position on said support panel to enable the radiation beam to be directed to that portion of the patient, the portion of the patient being held at the fixed position on said support panel by use of said fixation device, said support panel having peripheral edge of a predetermined shape which is bulbous in cross section and having undercut surface, said fixation device comprising a flexible planar thermoplastic sheet having two opposed side portions, a first frame member fixedly secured to one of said side portions and a second frame member fixedly secured to the other of said side portions, said first frame member having a first portion of generally C-shape in cross-section for snap-fit engagement with said peripheral edge of said support panel, said first portion of said first frame member being arranged to be flexed open to receive a first portion of the periphery of said support panel therein and then snap-fit closed, whereupon said first portion of the periphery of said support panel is snap-fit within said first portion of said first frame member, said second frame member having a second portion of generally C-shape in cross-section for snap-fit engagement with said peripheral edge of said support panel, said second portion of said second frame member being arranged to be flexed open to receive a second portion of the periphery of said support panel therein and then snap-fit closed, whereupon said second portion of the periphery of said support panel is snap-fit within said second portion of said second frame member, each of said first and second frame members including a peripheral free edge portion arranged to be snap-fit into a respective portion of said undercut surface of said peripheral edge of said support panel to hold said fixation device at a fixed position on said support panel, said fixation device being arranged to be removed from said support panel when desired by flexing said first and second portions of said first and second frame members open to release the respective portions of the periphery of said support panel therefrom and then to be resecured to said support panel at said fixed position when desired, said fixation device exhibiting a uniform density which does not result in any attenuation discontinuities of a radiation beam passing therethrough.

14. The system of claim 13 wherein said thermoplastic sheet is arranged to be heated to render it conformable and stretchable, whereupon said fixation device can be stretched across a portion of the body of the patient by pulling on said first and second frame members so that said flexible sheet conforms to the shape of that portion of the body of the patient.

15. The system of claim 13 wherein said thermoplastic sheet is shaped to accommodate the head of a patient.

16. The system of claim 15 wherein said thermoplastic sheet is perforated.

17. The system of claim 13 wherein said thermoplastic sheet is shaped to accommodate the head and shoulders of a patient.

18. A fixation device for use with a support panel for supporting a patient for radiation therapy, the support panel comprising a generally planar member arranged to be disposed adjacent an apparatus for producing a radiation beam to hold a portion of a patient at a fixed position on the support panel to enable the radiation beam to be directed to that portion of the patient, the support panel having peripheral edge of a predetermined shape which is bulbous in cross section and has an undercut surface, said fixation device comprising a flexible planar thermoplastic sheet having two opposed side portions, a first frame member fixedly secured to one of said side portions and a second frame member fixedly secured to the other of said side portions, said first frame member having a first portion of generally C-shape in cross-section for snap-fit engagement with the peripheral edge of the support panel, said first portion of said first frame member being arranged to be flexed open to receive a first portion of the peripheral edge of the support panel therein and then snap-fit closed, whereupon the first portion of the peripheral edge of the support panel is snap-fit within said first portion of said first frame member, said second frame member having a second portion of generally C-shape in cross-section for snap-fit engagement with the peripheral edge of the support panel, said second portion of said second frame member being arranged to be flexed open to receive a second portion of the peripheral edge of the support panel therein and then snap-fit closed, whereupon the second portion of the periphery of the support panel is snap-fit within said second portion of said second frame member, each of said first and second frame members including a peripheral free edge portion arranged to be snap-fit into a respective portion of the undercut surface of the peripheral edge of the support panel to hold said fixation device at a fixed position on the support panel, said fixation device being arranged to be removed from the support panel when desired by flexing said first and second portions of said first and second frame members open to release the respective portions of the periphery of said support panel therefrom and then to be resecured to the support panel at said fixed position when desired, said fixation device exhibiting a uniform density which does not result in any attenuation discontinuities of a radiation beam passing therethrough.

19. The fixation device of claim 18 wherein said thermoplastic sheet is arranged to be heated to render it conformable and stretchable, whereupon said fixation device can be stretched across a portion of the body of the patient by pulling on said first and second frame members so that said flexible sheet conforms to the shape of that portion of the body of the patient.

20. The fixation device of claim 18 wherein said thermoplastic sheet is shaped to accommodate the head of a patient.

21. The fixation device of claim 20 wherein said thermoplastic sheet is perforated.

22. The fixation device of claim 18 wherein said thermoplastic sheet is shaped to accommodate the head and shoulders of a patient.

* * * * *